United States Patent
Biondo et al.

(10) Patent No.: US 9,797,881 B2
(45) Date of Patent: Oct. 24, 2017

(54) METHOD AND SYSTEM FOR CONTROLLING A PASSIVE DRIVER IMPAIRMENT DETECTION SYSTEM IN A VEHICLE

(71) Applicant: GM GLOBAL TECHNOLOGY OPERATIONS LLC, Detroit, MI (US)

(72) Inventors: William A. Biondo, Beverly Hills, MI (US); David T. Proefke, Troy, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 90 days.

(21) Appl. No.: 14/933,326

(22) Filed: Nov. 5, 2015

(65) Prior Publication Data
US 2017/0131261 A1 May 11, 2017

(51) Int. Cl.
| | |
|---|---|
| G08B 23/00 | (2006.01) |
| G01N 33/497 | (2006.01) |
| B60R 16/03 | (2006.01) |
| F02N 11/08 | (2006.01) |
| G01N 33/00 | (2006.01) |
| B60K 28/00 | (2006.01) |
| A61B 5/00 | (2006.01) |
| A61B 5/087 | (2006.01) |

(52) U.S. Cl.
CPC ....... *G01N 33/4972* (2013.01); *A61B 5/0873* (2013.01); *A61B 5/4845* (2013.01); *A61B 5/6893* (2013.01); *B60K 28/00* (2013.01); *B60R 16/03* (2013.01); *F02N 11/0807* (2013.01); *G01N 33/0073* (2013.01)

(58) Field of Classification Search
CPC ................ B60K 28/06; A60W 40/08
USPC ........................................... 340/576
See application file for complete search history.

(56) References Cited

U.S. PATENT DOCUMENTS

| | | | |
|---|---|---|---|
| 2005/0030184 A1* | 2/2005 | Victor | B60K 28/06 340/576 |
| 2011/0284304 A1* | 11/2011 | Van Schoiack | B62D 1/046 180/272 |

(Continued)

OTHER PUBLICATIONS

Breath-Based Technology, website, www.dadss.org (Driver Alcohol Detection System for Safety), 2 pages.

(Continued)

*Primary Examiner* — Fabricio R Murillo Garcia
(74) *Attorney, Agent, or Firm* — Reising Ethington, P.C.

(57) ABSTRACT

Methods and systems for controlling a passive driver impairment detection system in a vehicle are provided. The method and system detect states of vehicle component operating systems and/or vehicle occupant monitoring systems and control activation and deactivation of the impairment detection system in response. The methods and systems enable a proactive transition from an inactive state to an active state by detecting the presence of an individual within or approaching the vehicle or an intent of the individual to approach the vehicle in order to overcome a significant functional latency in the impairment detection system. The methods and system further enable a transition from the active state to the inactive state by using multiple systems to corroborate the absence of the individual within or approaching the vehicle and the lack of intent of the individual to approach the vehicle.

23 Claims, 4 Drawing Sheets

(56) References Cited

U.S. PATENT DOCUMENTS

2014/0231166 A1* 8/2014 Miller ................... B60W 40/08
  180/272
2015/0216466 A1* 8/2015 Kronberg ................ A61B 5/18
  702/19

OTHER PUBLICATIONS

Touch-Based Technology, website, www.dadss.org (Driver Alcohol Detection System for Safety), 2 pages.

* cited by examiner

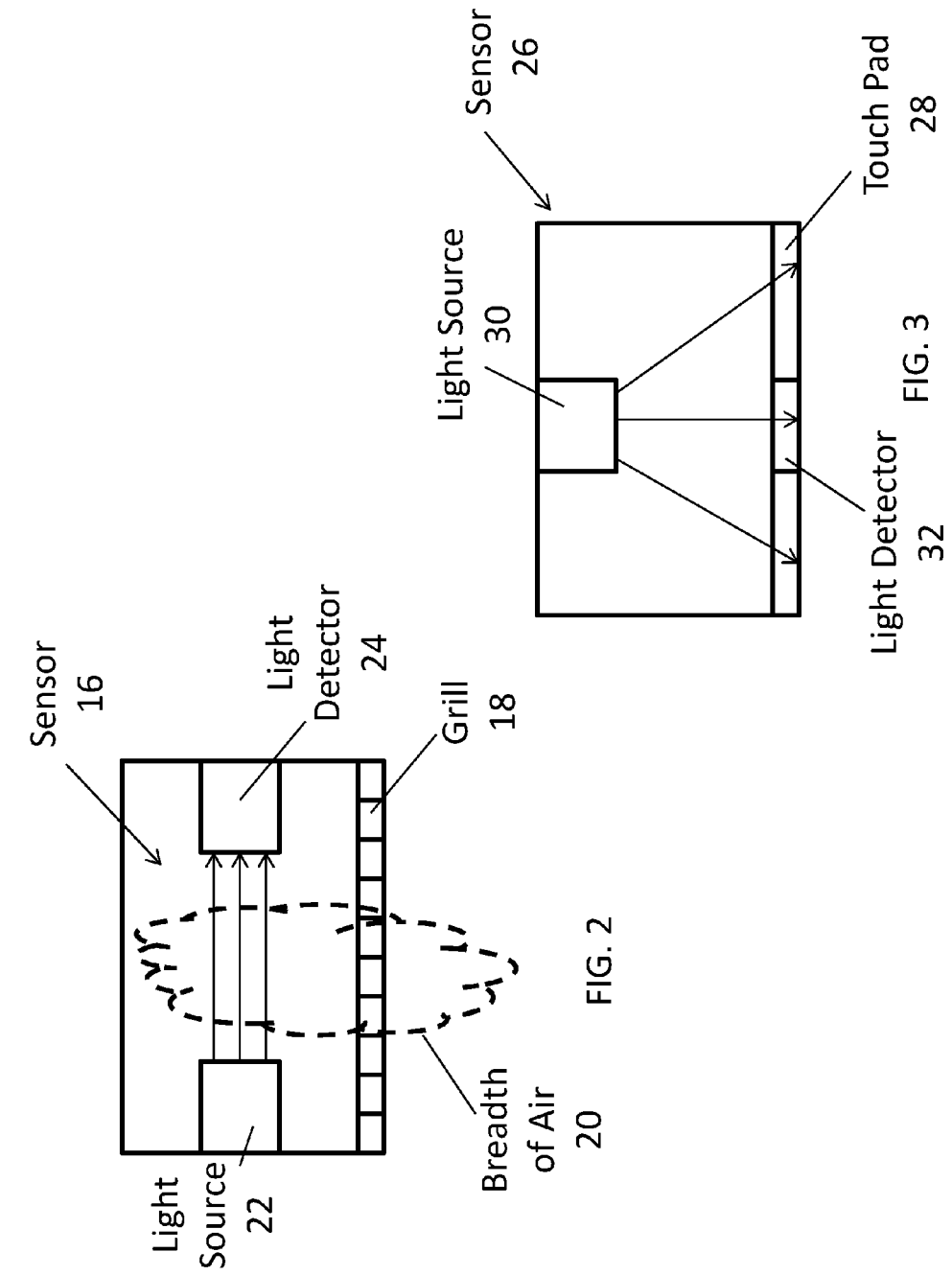

METHOD AND SYSTEM FOR CONTROLLING A PASSIVE DRIVER IMPAIRMENT DETECTION SYSTEM IN A VEHICLE

FIELD

The present invention relates generally to a vehicle system. More specifically, the invention relates to a method and system for controlling a passive driver impairment detection system in a vehicle.

BACKGROUND

It is well recognized that alcohol, medications and legal and illegal drugs can impair a person's ability to safely operate a vehicle. To address impairments resulting from alcohol intoxication, devices such as ignition interlock devices have been developed that require drivers to perform various actions before the vehicle's ignition system will operate. Current devices are considered active driver impairment detection devices because the devices require substantive actions by the driver to initiate and/or operate the systems. For example, many current devices require the driver to insert a tube into the driver's mouth and exhale a breath into the tube so that the device can detect the blood alcohol content of the driver. Ignition interlock devices are typically used when a driver has been convicted of a crime involving prior operation of a vehicle while impaired. Although use of the devices is inconvenient for the driver, the inconvenience is considered to be a reasonable part of the punishment for the crime committed by the driver.

In recent years, interest has grown in a passive driver impairment detection system that that could be used as standard equipment in vehicles to guard against impaired driving by the general population (i.e. including the vast majority of drivers who have not been convicted of crimes resulting from impaired driving). It is desirable to develop a driver impairment detection system that can detect driver impairments with little or no action by the driver to initiate or operate the system and thereby minimize any inconvenience to drivers and spur wide scale adoption and use of the system. Unfortunately, passive driver impairment detection systems that have been developed to date suffer from several deficiencies. The systems rely on lasers that require a relatively significant amount of time after power is first delivered to reach an operational stage. The systems therefore continue to be inconvenient for drivers. The systems may also power down and become inactive in situations where it would be desirable to maintain an active state (e.g., while a vehicle is temporarily stopped to allow a driver to watch an event from the vehicle).

SUMMARY

According to one embodiment, there is provided a method for controlling a passive driver impairment detection system in a vehicle. The method may include detecting a state of a first vehicle system indicative of a presence of an individual within or approaching the vehicle or an intent of the individual to approach the vehicle. The method may further include transmitting an activation signal to the passive driver impairment detection system upon detection of the state indicative of the presence of the individual within or approaching the vehicle or the intent of the individual to approach the vehicle, the passive driver impairment detection system having a significant functional latency. The method may further include proactively transitioning the passive driver impairment detection system from an inactive state to an active state responsive to the activation signal. The transition from the inactive state to the active state results in an apparent reduction to the individual of the significant functional latency of the passive driver impairment detection system.

According to another embodiment, there is provided a method for controlling a passive driver impairment detection system in a vehicle. The method may include detecting states of a vehicle component operating system and a vehicle occupant monitoring system indicative of an absence of an individual within or approaching the vehicle and a lack of intent of the individual to approach the vehicle. The method may further include transmitting a deactivation signal to the passive driver impairment detection system upon detection of the states of the vehicle component operating system and the vehicle occupant monitoring system indicative of the absence of the individual within or approaching the vehicle and the lack of intent of the individual to approach the vehicle. The method may further include transitioning the passive driver impairment detection system from an active state to an inactive state responsive to the deactivation signal. The transition from the active state to the inactive state only occurs when the states of the vehicle component operating system and the vehicle occupant monitoring system indicative of the absence of the individual within or approaching the vehicle and the lack of intent of the individual to approach the vehicle corroborate each other and confirm the absence of the individual within or approaching the vehicle and the lack of intent of the individual to approach the vehicle.

According to another embodiment, there is provided a method for controlling a passive driver impairment detection system in a vehicle. The method may include detecting an off state of a vehicle ignition system. The off state of the vehicle ignition system is indicative of an absence of an individual within or approaching the vehicle and a lack of intent of the individual to approach the vehicle. The method may further include detecting an inactive state of a vehicle remote starting system. The inactive state of the vehicle remote starting system is indicative of the absence of the individual within or approaching the vehicle and the lack of intent of the individual to approach the vehicle. The method may further include transmitting a deactivation signal to the passive driver impairment detection system upon detection of the off state of the vehicle ignition system and the inactive state of the vehicle remote starting system and transitioning the passive driver impairment detection system from an active state to an inactive state responsive to the deactivation signal. The transition from the active state to the inactive state only occurs when the off state of the vehicle ignition system and the inactive state of the vehicle remote starting system corroborate each other and confirm the absence of the individual within or approaching the vehicle and the lack of intent of the individual to approach the vehicle.

DRAWINGS

Preferred exemplary embodiments will hereinafter be described in conjunction with the appended drawings, wherein like designations denote like elements, and wherein:

FIGS. 2-3 are schematic views of two embodiments of a passive driver impairment detection system.

DESCRIPTION

Figure 1:
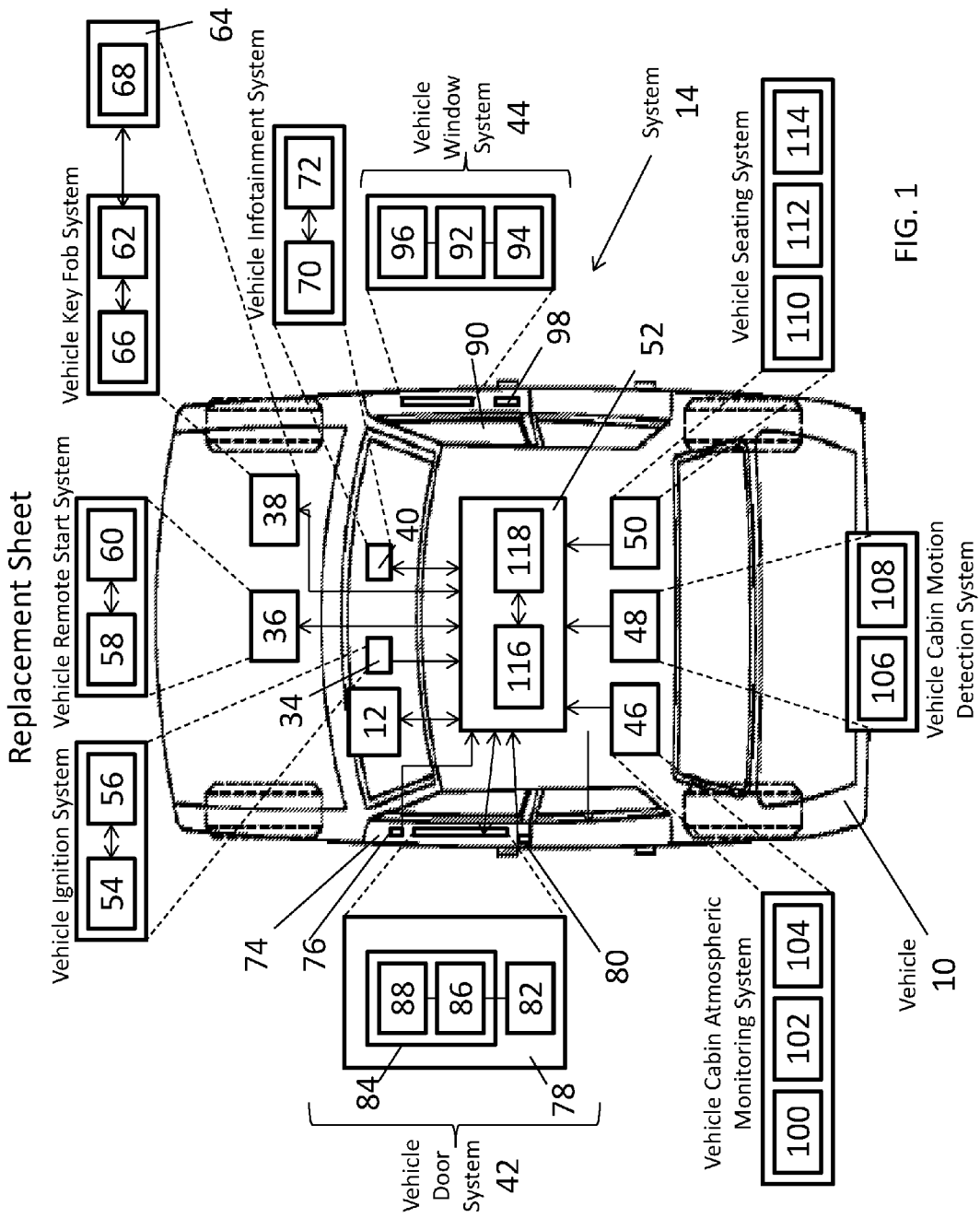
FIG. 1 is a schematic view of a vehicle including one embodiment of a system for controlling a passive driver impairment detection system in the vehicle.

Referring now to the drawings wherein like reference numerals are used to identify identical components in the various views, FIG. 1 illustrates a vehicle 10 including a passive driver impairment system 12 and one embodiment of a system 14 for controlling the passive driver impairment detection system 12. Although certain aspects of the description and illustration of vehicle 10 herein pertain to a vehicle having an internal combustion engine, it should be understood that systems 12 and 14 may be adapted for use with any type of vehicle, including hybrid electric vehicles (HEVs), extended-range electric vehicles (EREVs), battery electrical vehicles (BEVs), motorcycles, passenger vehicles, sports utility vehicles (SUVs), cross-over vehicles, trucks, vans, buses, recreational vehicles (RVs), etc.

Passive driver impairment detection system 12 is provided to detect an impairment of the driver. As used herein, a "passive" driver impairment detection system is one that requires limited or no action on the part of the driver to initiate and operate the system 12 and is contrasted with "active" driver impairment detection systems such as conventional ignition interlock devices that require the driver to, for example, insert a tube into the driver's mouth and exhale a breath into the tube. Referring to FIG. 2, system 12 may, for example, comprise a breath-based system that pulls or draws a breath of exhaled air from the driver (i.e. without requiring the driver to actively push or force a breath of air into a tube) and analyzes molecules in the breath of air to determine blood alcohol content. The system includes a sensor 16 that may be mounted on, for example, the steering column or driver side door. The sensor 16 may include a grill 18 through which a breath of air 20 is drawn, a light source 22 such as a laser that generates beams of light and directs the light through the breath of air 20, and a light detector 24 that receives light after interaction with the breath of air 20. Because alcohol and carbon dioxide molecules in the breath of air 20 absorb different amounts of the generated light, the sensor 16 is able to compare the amount of light received, determine the amount of alcohol molecules in the breath of air 20 and determine blood alcohol content in response, and then determine whether the blood alcohol content exceeds a predetermined level. Referring to FIG. 3, system 12 may alternatively comprise a touch-based system. The system includes a sensor 26 that may be incorporated into a gear shift lever, steering wheel, or into an ignition button mounted on, for example, the instrument panel (i.e. dashboard) of the vehicle. The sensor 26 includes a touchpad 28 that the driver touches as the driver attempts to shift gears, steer, or start the vehicle ignition system. The sensor 26 further includes a light source 30 such as a laser that generates beams of light and directs the light towards the skin surface of the driver and into skin tissues of the driver and a light detector 32 that detects light reflected back from the tissues to the skin surface. Because alcohol and other impairment causing compounds absorb specific wavelengths of the generated light, the sensor 26 is able to analyze the light received at detector 32 and determine blood alcohol content and whether the blood alcohol content exceeds a predetermined level. Passive driver impairment detection systems 12 of the type illustrated in FIGS. 2-3 have a significant functional latency. Once power is provided to system 12, the light sources 22, 30, respectively, require a period of time to "warm up" and reach an operational state. As a result, the driver is unable to operate the vehicle 10 until this period of time passes and system 12 reaches an operational state. The delay is an inconvenience to the driver and may discourage wide adoption and use of system 12. As used herein, "significant functional latency" refers to a time period of about one second or more.

System 14 is provided to control the passive driver impairment detection system 12 and, in accordance with one aspect of the invention, to cause an apparent reduction to the driver of the significant functional latency of system 12. System 14 may include various vehicle systems having states that are indicative of the presence or absence of an individual within or approaching vehicle 10 or the intent or lack of intent of the individual to approach vehicle 10. These vehicle systems may include vehicle component operating systems such as a vehicle ignition system 34, a vehicle remote start system 36, a vehicle key fob system 38, a vehicle infotainment system 40, a vehicle door system 42, and a vehicle window system 44. The vehicle systems may also include vehicle occupant monitoring systems such as a vehicle cabin atmospheric monitoring system 46, a vehicle cabin motion detection system 48, and a vehicle seating system 50. Although the illustrated vehicle systems form part of vehicle 10, it should be understood that vehicle systems on other vehicles that are capable of direct or indirect vehicle to vehicle communication with vehicle 10 could also assume states that are indicative of the presence or absence of an individual within or approaching vehicle 10 or the intent or lack of intent of the individual to approach vehicle 10. Further, it should be understood that vehicle systems other than those specifically illustrated and/or described herein may also have states that are indicative of the presence or absence of an individual within or approaching the vehicle or the intent or lack of intent of the individual to approach vehicle 10. System 14 further includes a controller 52 configured to control passive driver impairment detection system 12 in response to the current states of one or more of the vehicle systems 34, 36, 38, 40, 42, 44, 46, 48, 50.

Each of the vehicle systems 34, 36, 38, 40, 42, 44, 46, 48, 50 described herein will typically include one or more sensors that provide, or are indirectly capable of providing, an output indicative of a state of the vehicle system 34, 36, 38, 40, 42, 44, 46, 48, 50. The sensors may be embodied in hardware, software, firmware or some combination thereof. The sensors may directly sense or measure the conditions for which they are provided, or they may indirectly evaluate such conditions based on information provided by other sensors, components, devices, modules, systems, etc. The sensors may be directly coupled to controller 52, indirectly coupled via other electronic devices, a vehicle communications bus, network, etc., or coupled according to some other arrangement known in the art. The sensors may also be integrated within another vehicle component, device, module, system, etc., may be stand-alone components, or they may be provided according to some other arrangement. In some instances, multiple sensors might be employed to sense a single parameter (e.g., for providing redundancy). The sensors may employ variety of different sensing techniques depending on the application including, for example, optical, sound, electromagnetic or other sensing technologies. The information conveyed by the signals may be absolute in nature or relative in nature.

Vehicle ignition system 34 controls the delivery of electric power from a vehicle battery to accessory systems such as infotainment system 40, window system 44 and the vehicle lighting system. System 34 also controls the delivery of electric power from the battery to the fuel system (including the fuel pump and fuel injection system), the ignition system and the starter motor. System 34 includes an electronic switch 54 and an actuator 56 such as a key lock cylinder, pushbutton or rotary element that is used to control the position of the electronic switch 54 and is typically located on the vehicle instrument panel or steering column. A controller (e.g., a body control module) translates actuation of the switch 54 into commands used to control delivery of electric power. The ignition system 34 has an off state (when the actuator 56 is in the off position) and an on state (when the actuator 56 is in any of the accessory, on or start positions) and may include a sensor (not shown) that generates an output indicative of these states (and/or positions). The off state may be indicative of the absence of an individual within or approaching the vehicle 10 and a lack of intent of the individual to approach the vehicle 10. The on state may be indicative of the presence of the individual within or approaching the vehicle 10 or an intent of the individual to approach the vehicle 10.

Remote start system 36 is provided to enable the vehicle 10 to be started without use of ignition system 34 and typically from a location remote from the vehicle 10. System 36 may include a wireless transceiver 58 configured to receive remote start command signals generated by another wireless transmitter or transceiver in a key fob or similar device. System 36 may also include a processor 60 that is configured to activate a starter motor when the wireless transceiver 58 receives a remote start command signal. The processor 60 may also be configured to receive remote start command signals sent through a vehicle telematics unit (e.g., those generated using a mobile communications device such as a cellular phone). The remote start system 36 has an inactive state (in the absence of any remote start command signal) and an active state (when acting in response to receipt of a remote start command signal). The inactive state is indicative of the absence of an individual within or approaching the vehicle 10 and the lack of intent of the individual to approach the vehicle 10. The active state is indicative of the presence of the individual within or approaching the vehicle 10 or the intent of the individual to approach the vehicle 10.

Vehicle key fob system 38 is provided to enable remote starts of vehicle 10 and remote control of other vehicle components including door locks and a rear closure release system. Key fob system 38 may comprise part of a passive entry, passive start (PEPS) system. Key fob system 38 may include a wireless receiver or transceiver 62 configured to receive command signals generated by another wireless transmitter or transceiver in a key fob 64 or similar device. System 38 may also include a processor 66 that is configured to generate and transmit control signals to vehicle components such as door locks and a rear closure release system. It should be understood that vehicle key fob system 38 may incorporate remote start system 36. Key fob system 36 may have states defined by the actuation of the key fob 64 and the distance of the key fob 64 from the vehicle 10. In particular, actuation of an actuator 68 on the key fob 64 is indicative of the presence of an individual within or approaching the vehicle 10 or the intent of the individual to approach the vehicle 10 while the lack of actuation of the actuator 68 is indicative of the absence of the individual within or approaching the vehicle 10 and a lack of intent of the individual to approach the vehicle 10. Similarly, a key fob 64 that is nearer to the vehicle 10 (as indicated, for example, by the strength of a transmitted signal) is indicative of the presence of the individual within or approaching the vehicle 10 or the intent of the individual to approach the vehicle 10 while a key fob 64 that is further away from the vehicle 10 is indicative of the absence of the individual within or approaching the vehicle 10 and the lack of intent of the individual to approach the vehicle 10.

Vehicle infotainment system 40 provides information and entertainment to the driver and other occupants of vehicle 10. System 40 may include a user interface 70 and a communications module 72. User interface 70 may include any combination of hardware, software and/or other components that enable a vehicle occupant to exchange information or data with the vehicle. This includes, for example, input components like a touch-screen display, a microphone, a keyboard, a pushbutton or other control where user interface 70 receives information from a vehicle occupant, as well as output components like a visual display, an instrument panel, or an audio system where user interface 70 provides information to the vehicle occupant. In some cases, user interface 70 includes components with both input and output capabilities, such as visual and audible interfaces. The audible interface may be part of an automated voice processing system that uses voice-recognition and/or other human-machine interface (HMI) technology. User interface 70 may be mounted on a dashboard (e.g., with a driver information center (DIC)); it may be projected onto a windshield (e.g., with a heads-up display); it may be integrated within an existing audio system; or it may simply include an electronic connection or port for connecting with a smartphone, laptop or other computing device, to cite a few examples. Communications module 72 may include any combination of hardware, software and/or other components that enable wireless voice and/or data communication between the vehicle and some other entity. According to one exemplary embodiment, communications module 72 includes a voice interface, a data interface and a GPS receiver, and may be bundled or integrated within a device such as a telematics unit. The voice interface enables voice communication to and/or from vehicle 10 and may include a cellular chipset (e.g., CDMA or GSM chipset), a vocoder, voice over IP (VOIP) equipment, and/or any other suitable device. The data interface, on the other hand, enables data communication to and/or from vehicle 10 and may include a modem (e.g., a modem using EVDO, CDMA, GPRS or EDGE technologies), a wireless networking component (e.g., one using an IEEE 802.11 protocol, WiMAX, BluTooth, etc.), or any other suitable device. Depending on the particular embodiment, communications module 72 may communicate over a wireless carrier system (e.g., a cellular network), a wireless network (e.g., a wireless LAN, WAN, etc.), or some other wireless medium. The GPS receiver may receive signals from a constellation of GPS satellites and use these signals to determine vehicle position, as is well understood in the art. Vehicle infotainment system 72 has an inactive state (when not in use) and an active state (when in use). The inactive state is indicative of the absence of an individual within or approaching the vehicle 10 and a lack of intent of the individual to approach the vehicle 10. The active state is indicative of the presence of the individual within or approaching the vehicle 10 or an intent of the individual to approach the vehicle 10.

Vehicle door system 42 is provided to control ingress to and egress from the cabin of vehicle 10. Door system 42 may include a vehicle door 74, a door switch 76, a door lock 78, and a door handle assembly 80.

Door 74 provides a barrier between the cabin of vehicle 10 and an exterior of vehicle 10. Door 74 is configured to seal an opening in the body of vehicle 10 and may be mounted to the body of vehicle 10 using one or more hinges. An exterior side of door 74 may be made from the same materials as the vehicle body (typically steel or aluminum). An interior side of door 74 may be made from plastic, wood, leather or other trim to match the interior surface of vehicle 10 and may define features such as an armrest, cup holders and receptacles for power door, window and mirror electronics. The exterior and interior sides of door 74 may define a space therebetween configured to house door lock 78 and a regulator for a window disposed in the door 74. Door 74 is movable between open and closed positions that may be indicative of the presence or absence of an individual within or approaching vehicle 10 or the intent or lack of intent of the individual to approach the vehicle 10. In particular, an open position of door 74 may be indicative of the presence of an individual within or approaching vehicle 10 or the intent of the individual to approach the vehicle 10 while a closed position of door 74 may be indicative of the absence of the individual within or approaching vehicle 10 and a lack of intent of the individual to approach the vehicle 10.

Door switch 76 is provided to activate an interior light or other audio or visual warning to vehicle occupants that a door is ajar (i.e. is in other than a closed position). Switch 76 may comprise a pushbutton switch that opens when actuated (when a door latch for door 74 is in a closed position) and closes when not actuated (when the door latch for door 74 is an open position). Door switch 76 may be coupled to controller 52. The position of door switch 76, because it indicates the position of the door latch for door 74, may be indicative of the presence or absence of an individual within or approaching the vehicle 10 or the intent or lack of intent of the individual to approach vehicle 10. In particular, the closed position of door switch 76 (when the door latch for door 74 is an open position) may be indicative of the presence of an individual within or approaching the vehicle 10 or the intent of the individual to approach the vehicle 10 while the open position of switch 76 (when a door latch for door 74 is in a closed position) may be indicative of the absence of the individual within or approaching the vehicle 10 or a lack of intent of the individual to approach the vehicle 10.

Door lock 78 controls ingress to and egress from vehicle 10 through door 74. Similar door locks may be used on each door of vehicle 10 and the door locks may be controlled together or independently by a controller such as controller 52. Door lock 78 may include a latch 82 and an actuator 84.

Latch 82 is provided to maintain door 74 in a closed position preventing ingress to or egress from the body of vehicle 10. Latch 82 engages a striker (not shown) when door 74 is closed. Latch 82 may be disengaged from, and reengaged with, the striker using a variety of mechanical means such as external and internal door handles and electro-mechanical means such as actuator 84.

Actuator 84 is provided to control movement of latch 82 to engage and disengage the striker in order to unlock and lock door 74. Actuator 84 may include a rod 86 that engages latch 82 and a motor 88 configured to control movement of rod 86 responsive to signals from controller 52. The signals generated by controller 52 may be generated in response to signals from a power door lock interface or key fobs. It should be understood that the particular construction of actuator 84 may vary.

Door handle assembly 80 provides a means for opening door 74 and causing movement of door 74 between open and closed positions. Assembly 80 may include separate handles on the exterior and interior of door. At least the door handle on the interior may be mechanically coupled to door lock 78 to cause door lock 78 to move from a locked state to an unlocked state as the door handle is moved. The door handles may assume a variety of forms including a traditional handle that may be moved by a user from an unactuated state (to which the handle may be biased when not in use) to an actuated state (when used to open door 74) or a pushbutton or keypad type handle likewise having an unactuated state (when the buttons or keys are not depressed or incorrectly pressed) and an actuated state (when the button or keys are properly pressed). The handles may alternatively comprise electronic sensors forming part of a passive entry passive start (PEPS) system that may be hidden behind the door panel or elsewhere on the vehicle and that are responsive to the presence of an individual or a device held by the individual. The sensors may likewise have an unactuated state (when inactive) and an actuated state (when activated by the presence of an individual or a device held by the individual). Assembly 80 may include one or more sensors coupled to controller 52 and configured to indicate the state of the exterior and/or interior door handles thereby providing an indication of the presence or absence of an individual within or approaching the vehicle 10 or the intent or lack of intent of the individual to approach the vehicle 10. In particular, the actuated state of a handle may be indicative of the presence of an individual within or approaching the vehicle 10 or the intent of the individual to approach the vehicle 10 while the unactuated state of a handle may be indicative of the absence of the individual within or approaching the vehicle 10 and the lack of intent of the individual to approach the vehicle 10.

Vehicle window system 44 enables vehicle occupants to see outside of the vehicle from the vehicle cabin and enables individuals to see inside the vehicle cabin from outside the vehicle. Vehicle window system 44 also provides a means for controlling the environment within the vehicle cabin. Window system 44 may include a window 90 typically made of glass, an electric motor 92, and a window regulator 94 that extends between the motor 92 and window 90 and controls the position of the window 90 responsive to movement of the motor 92. Window system 44 may further include a processor 96 that generates control signals to the motor 92 responsive to inputs from an actuator within the vehicle cabin or a key fob. Window system 44 may further include a position sensor 98 that detects whether the window 90 is open or closed (and possibly the position of the window 90) and thereby provides an indication of the presence or absence of an individual within or approaching the vehicle 10 or the intent or lack of intent of the individual to approach the vehicle 10. In particular, an open position or state of the window 90 may be indicative of the presence of an individual within or approaching the vehicle 10 or an intent of the individual to approach the vehicle 10 while a closed position or state of window 90 may be indicative of the absence of the individual within or approaching the vehicle 10 and a lack of intent of the individual to approach the vehicle 10.

Vehicle cabin atmospheric monitoring system 46 is provided to monitor the atmosphere within the vehicle cabin and to control that atmosphere. System 46 may therefore include a number of sensors for use in detecting atmospheric conditions within the vehicle including carbon dioxide sensors 100, temperature sensors 102 (such as infrared temperature sensors) and humidity sensors 104. Sensors 100, 102, 104 may provide indications of the presence or absence of an individual within or approaching the vehicle 10 or the intent or lack of intent of the individual to approach the vehicle 10. For example, the detection of a level of carbon dioxide above a predetermined level in the vehicle cabin may be indicative of the presence of an individual within the vehicle 10 while the a level of carbon dioxide below the predetermined level may be indicative of the absence of the individual from the vehicle 10. Detection of a temperature above a predetermined level (or an increase in temperature over time) may be indicative of the presence of an individual within or approaching the vehicle 10 or an intent of the individual to approach the vehicle while a temperature below the predetermined level (or a decrease in temperature over time) may be indicative of the absence of an individual within or approaching the vehicle 10 and the lack of intent of the individual to approach the vehicle. Detection of a difference in temperatures between the external ambient temperature and the internal vehicle cabin temperature (or a difference above a predetermined threshold temperature difference) may be indicative of the presence of an individual within or approaching the vehicle 10 or an intent of the individual to approach the vehicle while the lack of a difference (or a difference below a predetermined threshold temperature difference) may be indicative of the absence of an individual within or approaching the vehicle 10 and the lack of intent of the individual to approach the vehicle. Detection of a humidity above a predetermined level (or an increase in humidity) may be indicative of the presence of an individual within or approaching the vehicle 10 or an intent of the individual to approach the vehicle while a humidity below the predetermined level (or a decrease in humidity over time) may be indicative of the absence of an individual within or approaching the vehicle 10 and a lack of intent of the individual to approach the vehicle.

Vehicle cabin motion detection system 48 is used to provide an indication of the presence of a person or animal within the vehicle cabin. For example, the system 48 can be used to alert a driver to a small child or animal unintentionally left within the vehicle cabin. System 48 can also alert a vehicle owner to unauthorized entry into the vehicle. System 48 may include motion or inclination sensors 106 and/or a camera 108. Motion detected by the sensors 106 or camera 108 may be indicative of the presence of an individual within or approaching the vehicle 10 or an intent of the individual to approach the vehicle 10 while the absence of motion detection by the sensors 106 or camera 108 may be indicative of the absence of the individual within or approaching the vehicle 10 and a lack of intent of the individual to approach the vehicle 10.

Vehicle seating system 50 is provided to seat a vehicle occupant within the vehicle 10 and position the occupant relative to other vehicle components within the vehicle cabin such as the steering column. System 50 may include a seat 110, a safety belt 112 for securing an individual in the seat 110, and one more mechanical or electronic ("power") controls for adjusting the position of the seat 110 (i.e. up or down, forward back degree of recline, etc.). System 50 may further include one or more sensors 114 configured to sense, for example, the presence of a vehicle occupant occupying the seat, the position of the seat, and the use of the safety belt. The output of these sensors 114 may be indicative of the presence or absence of an individual within or approaching the vehicle 10. For example, a sensor output indicating that presence of an object in the seat 110 may be indicative of the presence of an individual within or approaching the vehicle 10 or an intent of the individual to approach the vehicle 10 while a sensor output indicating the absence of an object in the seat 110 may be indicative of the absence of an individual within or approaching the vehicle 10 and a lack of intent of the individual to approach the vehicle. A sensor output indicating movement of the position of the seat 110 may be indicative of the presence of an individual within or approaching the vehicle 10 or an intent of the individual to approach the vehicle 10 while the lack of such an output may be indicative of the absence of an individual within or approaching the vehicle 10 and a lack of intent of the individual to approach the vehicle 10. A sensor output indicating that the safety belt 112 has been moved and or buckled may be indicative of the presence of an individual within or approaching the vehicle 10 or an intent of the individual to approach the vehicle 10 while the lack of such an output may be indicative of the absence of an individual within or approaching the vehicle 10 and a lack of intent of the individual to approach the vehicle 10.

Controller 52 processes signals generated by sensors associated with systems 34, 36, 38, 40, 42, 44, 46, 48, 50 and is configured to control passive driver impairment detection system 12 in response to the state of one or more of the vehicle systems 34, 36, 38, 40, 42, 44, 46, 48, 50. Controller 52 may include a variety of electronic processing devices, memory devices, input/output (I/O) devices, and/or other known components, and may perform various control and/or communication related functions. In an exemplary embodiment, controller 52 includes an electronic memory device 116 that stores various sensor readings, look up tables or other data structures, software programs, etc. Memory device 116 may also store pertinent characteristics and background information pertaining to vehicle 10. Controller 52 may also include an electronic processing device 118 (e.g., a microprocessor, a microcontroller, an application specific integrated circuit (ASIC), etc.) that executes instructions for software, firmware, programs, algorithms, scripts, etc. that are stored in memory device 116. Controller 52 may also include an input/output interface through which controller 52 may receive input signals including signals generated by systems 34, 36, 38, 40, 42, 44, 46, 48, 50 and generate output signals including those used to control passive driver impairment detection system 12. Depending on the particular embodiment, controller 52 may be a stand-alone vehicle electronic module, it may be incorporated or included within another vehicle electronic module, or it may be part of a larger network or system. Controller 52 may be electronically connected to other vehicle devices, modules and systems via a vehicle communications bus or other communication means and can interact with them when required.

Figure 4:
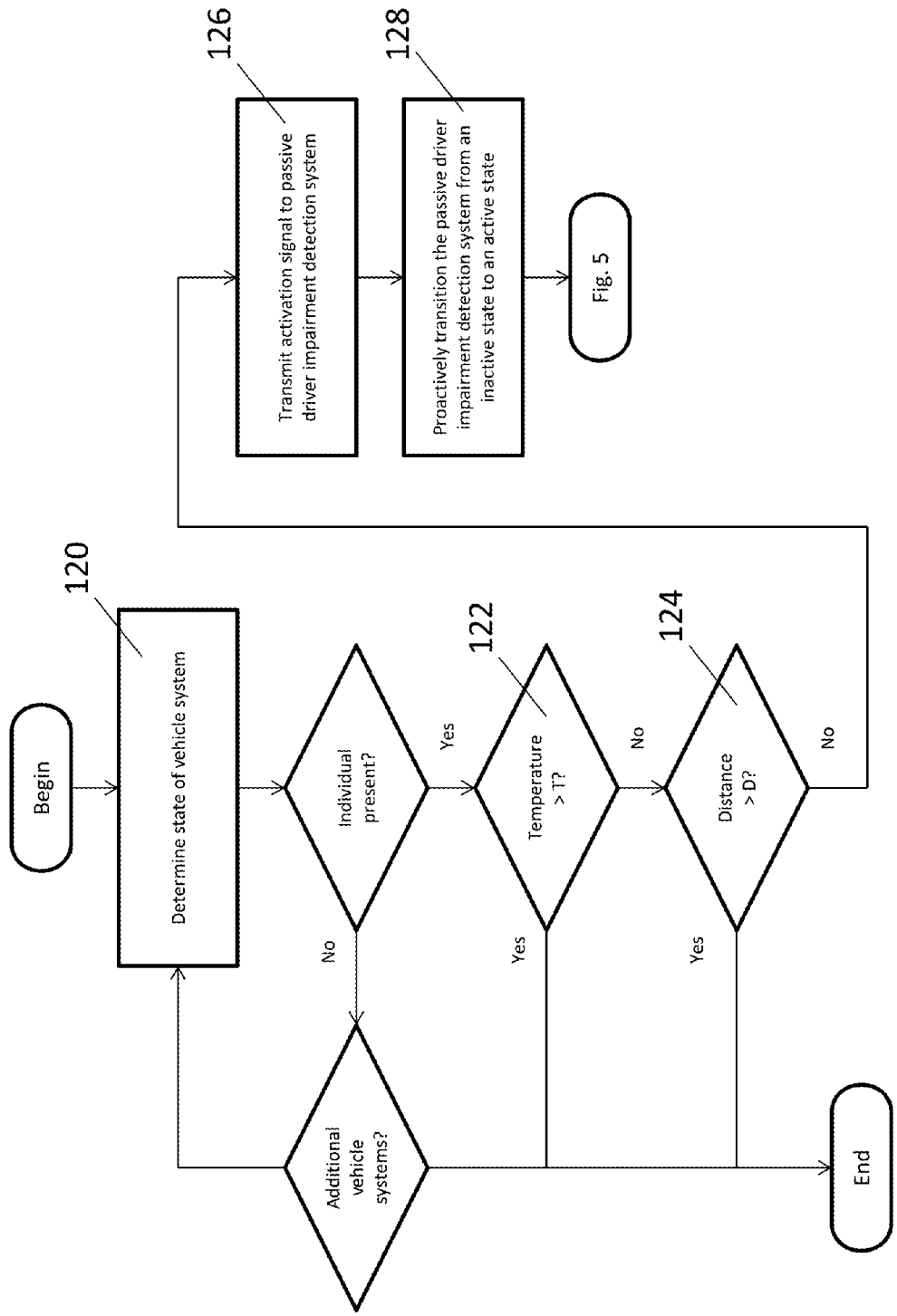
FIGS. 4-5 are flowcharts illustrating embodiments of a method for controlling a passive driver impairment detection system in a vehicle.

In accordance with one embodiment, controller 52 is configured with appropriate programming instructions or code (i.e., software) to perform several steps in a method for controlling passive driver impairment detection system 12. The code may be stored in memory device 116 of controller 52 and may be uploaded to memory device 116 from, a conventional computer storage medium. Referring now to FIG. 4, the method may include several steps associated with transitioning system from an inactive state to an active state with an apparent reduction in the functional latency of the system 12 to a user. The method may include the step 120 of detecting a state of a vehicle system indicative of the presence of an individual within or approaching the vehicle 10 or an intent of the individual to approach the vehicle 10. As set forth above, a number of vehicle systems may have states that are indicative of the presence of an individual within or approaching vehicle 10 or an intent of the individual to approach the vehicle 10 including systems 34, 36, 38, 40, 42, 44, 46, 48, 50. Controller 52 may detect a state of a vehicle system indicative of the presence of an individual within or approaching the vehicle 10 or an intent of the individual to approach the vehicle 10 based on the output of one or more sensors in the system that are indicative of the state. Because one of the goals of a method in accordance with the present teachings is to activate passive driver impairment detection system 12 earlier in time and encourage adoption of system 12, controller 52 may be configured to review sensor outputs from a plurality of vehicle systems and to performs steps to activate system 12 if any of the vehicle systems indicate the presence of an individual within or approaching the vehicle 10 or an intent of the individual to approach the vehicle 10. Therefore, as illustrated in FIG. 3, if a particular vehicle system does not indicate the presence of an individual, controller 52 may examine the state of additional vehicle systems to determine if any other vehicle system indicates the presence of an individual within or approaching the vehicle 10 or an intent of the individual to approach the vehicle 10. Although FIG. 3 illustrates a successive review of vehicle systems, it should be understood that controller 52 may review sensor outputs from multiple systems simultaneously. In one embodiment, controller 52 may take steps to activate system 12 if any of the following conditions are true: vehicle ignition system 34 is an on state, a door 74 of vehicle door system 42 is in an open position, remote start system 36 is an active state, a key fob actuator 68 of vehicle key fob system 38 is in an actuated state, a handle of vehicle door system 42 in an actuated state or vehicle infotainment system 40 is in an active state.

If controller 52 detects a state of a vehicle system that indicates the presence of an individual within or approaching vehicle 10 or an intent of the individual to approach the vehicle 10, controller 52 may still determine that no action is required to activate system 12 in certain circumstances. As discussed hereinabove, several passive driver impairment detection systems rely on lasers or other components that have a significant functional latency. In particular, the components may require an undesirable amount of time between the moment when power is first provided and the time they achieve an operational state. In some cases, this time may be dependent on temperature—either of the component or the surrounding environment—and the latency problem may be eliminated or reduced if the temperature of the component or surrounding environment is already at a certain level. Therefore, in step 122, controller 52 may monitor the temperature in a location proximate the impairment detection system 12 and, if the temperature meets a predetermined condition relative to a predetermined temperature T (e.g., is greater than a predetermined temperature), controller 52 may refrain from taking action despite one or more vehicle systems indicating that an individual is within or approaching vehicle 10 or intends to approach the vehicle 10. Similarly, some vehicle systems may provide an indication that an individual remains a significant distance away from vehicle 10 such that activation of system 12 should not occur or be delayed until the individual is closer to vehicle 10. In particular, key fob system 38 may be configured such that a key fob 64 provides an indication of the distance of an approaching individual to the vehicle 10. Therefore, in step 124, controller 52 may determine a distance between the individual and vehicle 10 and, if the distance meets a predetermined condition relative to a predetermined distance D, controller 52 may refrain from, or delay, taking action despite one or more vehicle systems indicating the presence of an individual within or approaching the vehicle 10 or an intent of the individual to approach the vehicle 10.

Once controller 52 detects a state of a vehicle system indicative of the presence of an individual within or approaching vehicle 10 or an intent of the individual to approach the vehicle 10, controller 52 may perform the step 126 of transmitting an activation signal to passive driver impairment detection system 12. The activation signal is configured to cause system 12 to assume an active state. The method may further include the step 128 of proactively transitioning system 12 from an inactive state to an active state responsive to the activation signal. In particular, system 12 may switch from an inactive state to an active state upon receipt of the activation signal. The change in states is "proactive" in the sense that the transition occurs earlier in time than it ordinarily would and, in particular, before a vehicle driver would perform any action (such as inserting or turning a key in an ignition switch) normally relied upon to initiate conventional ignition interlock devices. Because the transition occurs earlier in time, the transition of system 12 from the inactive state to the active state results in an apparent reduction to driver of the significant functional latency of system 12.

Figure 5:
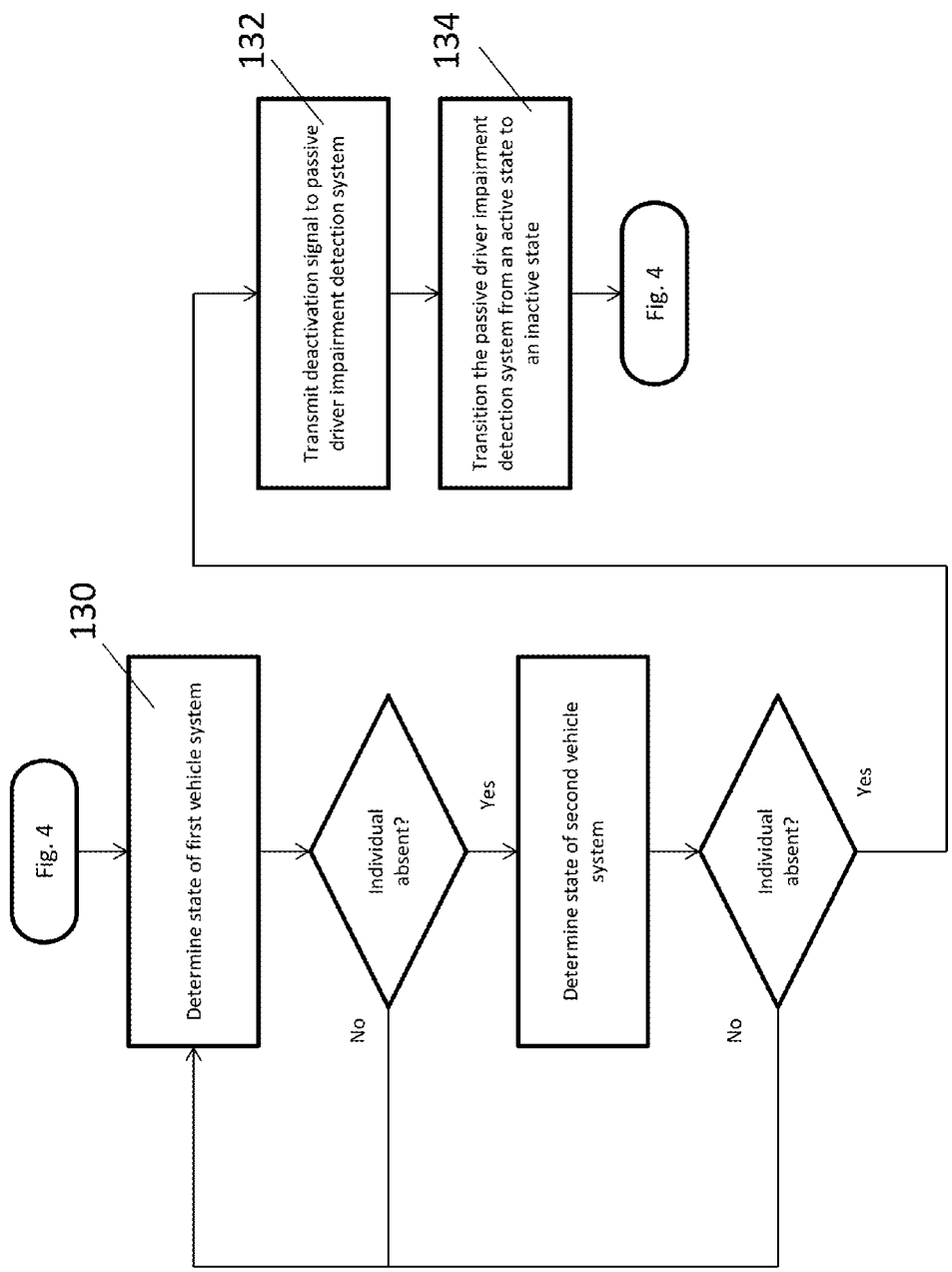

Referring now to FIG. 5, the method may further include several steps associated with transitioning system 12 from an active state to an inactive state. The method may include the step 130 of detecting a state of a vehicle system indicative of an absence of the individual within or approaching the vehicle 10 and a lack of intent of the individual to approach the vehicle 10. In accordance with certain embodiments of the invention, it may be desirable to require that multiple vehicle systems indicate the absence of an individual within or approaching the vehicle 10 and a lack of intent of the individual to approach the vehicle 10 and that these systems corroborate each other and confirm the absence of the individual within or approaching the vehicle 10 and a lack of intent of the individual to approach the vehicle 10. In this manner, system 12 will remain in an active state and is less likely to create an inconvenience to vehicle occupants (thereby discouraging adoption and use of system 12) despite variances in the manner in which vehicle 10 is used that might ordinarily result in transitioning system 12 to an inactive state. For example, a driver may temporarily park and/or turn off the vehicle 10, yet remain in the vehicle to watch a sporting event or perform another activity. By requiring multiple vehicle systems to indicate and corroborate the absence of an individual within or approaching the vehicle and a lack of intent of the individual to approach the vehicle 10, system 12 will remain active and available for immediate use during various uses of vehicle 10. Accordingly, as illustrated in FIG. 5, controller 52 may be configured to review sensor outputs from a plurality of vehicle systems and to performs steps to deactivate system 12 only if multiple vehicle systems indicate the absence of an individual within or approaching the vehicle and a lack of intent of the individual to approach the vehicle 10. Although FIG. 5 illustrates a successive review of vehicle systems, it should be understood that controller 52 may review sensor outputs from multiple systems simultaneously.

In one embodiment, controller 52 must detect states of both a vehicle component operating system (e.g., vehicle ignition system 34) and a vehicle occupant monitoring system (e.g., vehicle cabin atmospheric monitoring system 46) indicative of the absence of an individual within or approaching the vehicle 10 and a lack of intent of the individual to approach the vehicle 10 before taking steps to initiate a transition of system 12 to an inactive state. In another embodiment, controller 52 must detect an off state of vehicle ignition system 34 and an inactive state of vehicle remote starting system 36 before taking steps to initiate a transition of system 12 to an inactive state. In yet other embodiments, the controller 52 must detect not only the off state of the vehicle ignition system 34 and an inactive state of the vehicle remote starting system 36, but also detect one of the following three conditions or sets of conditions: (i) that the duration of time since the vehicle ignition system 34 entered the off state meets a predetermined condition (e.g., exceeds) a predetermined time (in which case the method may include the step of determining a duration since the vehicle ignition system 34 entered the off state); (ii) that (a) vehicle cabin atmospheric monitoring system 46 does not detect a carbon dioxide level above a predetermined level and (b) vehicle cabin motion detection system 48 does not detect any motion in the vehicle cabin and (c) vehicle seating system 50 indicates that the vehicle seat 110 is unoccupied or vehicle door system 42 indicates that the door 74 is locked and (d) that vehicle cabin atmospheric monitoring system 46 indicates a temperature above a predetermined temperature and (e) vehicle cabin motion detection system 48 does not detect the presence of a driver and (f) vehicle seating system 50 detects that the safety belt 112 is disengaged and (g) vehicle infotainment system 40 is inactive or (iii) that (a) vehicle window system 44 indicates that all windows 90 are closed and (b) vehicle door system 42 indicates that all doors 74 are closed and (c) vehicle key fob system 38 indicates that a key fob 64 is not within a predetermined distance of vehicle 10.

The method may further include the step 132 of transmitting a deactivation signal to passive driver impairment detection system 12 upon detection of states of various vehicle systems indicative of the absence of the individual within or approaching the vehicle 10 and a lack of intent of the individual to approach the vehicle 10. Controller 52 will transmit the deactivation signal to passive driver impairment detection system 12 once the states of multiple vehicle systems corroborate each other and confirm the absence of or an individual within or approaching the vehicle 10 and a lack of intent of the individual to approach the vehicle 10. For example, in certain embodiments, the state of both a vehicle component operating system and the vehicle occupant monitoring system must indicate the absence of the individual within or approaching the vehicle 10 and a lack of intent of the individual to approach the vehicle 10. In another embodiment, the absence of the individual within or approaching the vehicle 10 and a lack of intent of the individual to approach the vehicle 10 is indicated by both the off state of the vehicle ignition system 34 and the inactive state of the vehicle remote starting system 36. In yet another embodiment, the absence of the individual within or approaching the vehicle 10 and a lack of intent of the individual to approach the vehicle 10 also requires that the duration of time since the vehicle ignition system 34 entered the off state exceeds a predetermined duration.

The method may continue with the step 134 of transitioning the passive driver impairment detection system 12 from the active state to the inactive state responsive to the deactivation signal. As noted above, the transition may only occur when the states indicative of the absence of the individual within or approaching the vehicle 10 and a lack of intent of the individual to approach the vehicle 10 corroborate each other and confirm the absence of the individual within or approaching the vehicle 10 and a lack of intent of the individual to approach the vehicle 10. Again, these systems may comprise, for example, the vehicle component operating system and the vehicle occupant monitoring system. In another embodiment, the systems may include the vehicle ignition switch 34 and the vehicle remote starting system 36.

A system 14 and method for controlling a passive driver impairment detection system 12 in a vehicle 10 in accordance with the present teachings is advantageous relative to conventional methods and systems. In particular, the system 14 and method help to overcome a significant functional latency in passive driver impairment detection systems 12 by using a variety of vehicle systems to detect the presence of an individual within or approaching a vehicle 10 or an intent of the individual to approach the vehicle 10 to transition detection system from an inactive to an active state. In this manner, the detection system 12 reaches an operational state earlier in time such that the system is less likely to inconvenience a driver. As a result, wider adoption and use of the detection system is encouraged. Similarly, in certain embodiments the system 14 and method permit transition of the detection system 12 from the active state to an inactive state only when multiple vehicle systems corroborate the absence of an individual within or approaching the vehicle 10 and a lack of intent of the individual to approach the vehicle 10. As a result, the system 12 will remain active despite variations in use of the vehicle 10 and is again less likely to create an inconvenience to the driver that would discourage adoption and use of the system 12.

It is to be understood that the foregoing description is not a definition of the invention, but is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. For example, the specific combination and order of steps is just one possibility, as the present method may include a combination of steps that has fewer, greater or different steps than that shown here. All such other embodiments, changes, and modifications are intended to come within the scope of the appended claims.

As used in this specification and claims, the terms "for example," "e.g.," "for instance," "such as," and "like," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A method for controlling a passive driver impairment detection system in a vehicle, comprising the steps of:
    detecting a state of a first vehicle system, wherein the state of the first vehicle system includes an indication of at least one of the following: i) whether an individual is within the vehicle, ii) if not within the vehicle, whether the individual is approaching the vehicle, or iii) if not approaching the vehicle, whether the individual has an intent to approach the vehicle;
    transmitting an activation signal to the passive driver impairment detection system when detection of the state of the first vehicle system indicates at least one of i), ii) or iii), wherein the passive driver impairment detection system is provided to detect an impairment of the individual who intends to operate the vehicle and the passive driver impairment detection system has a significant functional latency; and proactively transitioning the passive driver impairment detection system from an inactive state to an active state responsive to the activation signal before the individual operates the vehicle;

wherein the transition from the inactive state to the active state results in a reduction, from the perspective of the individual, of the significant functional latency of the passive driver impairment detection system.

2. The method of claim 1, further comprising the steps of:
detecting a state of a second vehicle system indicative of the presence of the individual within or approaching the vehicle or the intent of the individual to approach the vehicle; and
transmitting the activation signal to the passive driver impairment detection system upon detection of the state of the second vehicle system indicative of the presence of the individual within or approaching the vehicle or the intent of the individual to approach the vehicle.

3. The method of claim 1, wherein the first vehicle system comprises a vehicle key fob system and the state of the first vehicle system indicative of the presence of the individual within or approaching the vehicle or the intent of the individual to approach the vehicle is one of a proximity of a key fob to the vehicle or actuation of an actuator of the key fob system.

4. The method of claim 1, wherein the first vehicle system comprises a vehicle door system and the state of the first vehicle system indicative of the presence of the individual within or approaching the vehicle or the intent of the individual to approach the vehicle is one of an open position of a door of the vehicle or an actuated state of a door handle of the door of the vehicle.

5. The method of claim 1, wherein the first vehicle system comprises a vehicle infotainment system and the state of the first vehicle system indicative of the presence of the individual within or approaching the vehicle is an active state of the vehicle infotainment system.

6. The method of claim 1, wherein the first vehicle system comprises a vehicle cabin atmospheric monitoring system having an infrared temperature sensor and the state of the first vehicle system indicative of the presence of the individual within or approaching the vehicle is a detection of a temperature above a predetermined temperature in a cabin of the vehicle.

7. The method of claim 1, wherein the first vehicle system comprises a vehicle cabin atmospheric monitoring system having a carbon dioxide sensor and the state of the first vehicle system indicative of the presence of the individual within or approaching the vehicle is a detection of a level of carbon dioxide above a predetermined level of carbon dioxide in a cabin of the vehicle.

8. The method of claim 1, wherein the passive driver impairment detection system comprises a touch-based system configured to direct light towards a tissue of the driver, determine blood alcohol content of the driver in response to the light received after interaction with the tissue, and determine whether the blood alcohol content exceeds a predetermined level.

9. The method of claim 1, wherein the passive driver impairment detection system comprises a breath-based system configured to draw a breath of exhaled air from the driver, direct a light through the breath of air, determine blood alcohol content of the driver in response to the light received after interaction with the breath of air, and determine whether the breath alcohol content exceeds a predetermined level.

10. The method of claim 1, further comprising the step of monitoring a temperature in a location proximate the passive driver impairment detection system and wherein the transmitting step comprises transmitting the activation signal only upon detection of the state indicative of the presence of the individual within or approaching the vehicle or the intent of the individual to approach the vehicle and the temperature meeting a predetermined condition relative to a predetermined temperature.

11. The method of claim 1, further comprising the step of determining a distance between the individual and the vehicle and wherein the transmitting step comprises transmitting the activation signal only upon detection of the state indicative of the presence of the individual within or approaching the vehicle or the intent of the individual to approach the vehicle and the distance meeting a predetermined condition relative to a predetermined distance.

12. The method of claim 1, further comprising the steps of:
detecting a state of the first vehicle system indicative of an absence of the individual within or approaching the vehicle and a lack of intent of the individual to approach the vehicle;
transmitting a deactivation signal to the passive driver impairment detection system upon detection of the state indicative of the absence of the individual within or approaching the vehicle and the lack of intent of the individual to approach the vehicle; and
transitioning the passive driver impairment detection system from the active state to the inactive state responsive to the deactivation signal.

13. The method of claim 1, wherein the first vehicle system comprises one system of a vehicle component operating system and a vehicle occupant monitoring system and further comprising the steps of:
detecting states of the one system and another system of the vehicle component operating system and the vehicle occupant monitoring system indicative of an absence of an individual within or approaching the vehicle and a lack of intent of the individual to approach the vehicle;
transmitting a deactivation signal to the passive driver impairment detection system upon detection of the states indicative of the absence of the individual within or approaching the vehicle and the lack of intent of the individual to approach the vehicle; and
transitioning the passive driver impairment detection system from an active state to an inactive state responsive to the deactivation signal;
wherein the transition from the active state to the inactive state only occurs when the states indicative of the absence of the individual within or approaching the vehicle and the lack of intent of the individual to approach the vehicle corroborate each other and confirm the absence of the individual within or approaching the vehicle and the lack of intent of the individual to approach the vehicle.

14. A method for controlling a passive driver impairment detection system in a vehicle, comprising the steps of:
detecting states of a vehicle component operating system and a vehicle occupant monitoring system, wherein the states include an indication of: i) an absence of an individual within or approaching the vehicle, and ii) a lack of intent of the individual to approach the vehicle;

transmitting a deactivation signal to the passive driver impairment detection system when detection of the states of the vehicle component operating system and the vehicle occupant monitoring system indicate i) and ii), wherein the passive driver impairment detection system is provided to detect an impairment of the individual who intends to operate the vehicle; and transitioning the passive driver impairment detection system from an active state to an inactive state responsive to the deactivation signal;

wherein the transition from the active state to the inactive state only occurs when both of the states of the vehicle component operating system and the vehicle occupant monitoring system corroborate each other and confirm i) and ii).

15. The method of claim 14, wherein the vehicle component operating system comprises a vehicle ignition system and the state of the vehicle component operating system indicative of the absence of the individual within or approaching the vehicle and the lack of intent of the individual to approach the vehicle is an off state of the vehicle ignition system.

16. The method of claim 14, wherein the vehicle component operating system comprises a vehicle remote starting system and the state of the vehicle component operating system indicative of the absence of the individual within or approaching the vehicle and the lack of intent of the individual to approach the vehicle is an inactive state of the vehicle remote starting system.

17. The method of claim 14, wherein the vehicle component operating system comprises a vehicle door system and the state of the vehicle component operating system indicative of the absence of the individual within or approaching the vehicle and the lack of intent of the individual to approach the vehicle is a closed position of a door of the vehicle and an unactuated state of a door handle of the door of the vehicle.

18. The method of claim 14, wherein the vehicle component operating system comprises a vehicle infotainment system and the state of the vehicle component operating system indicative of the absence of the individual within or approaching the vehicle and the lack of intent of the individual to approach the vehicle is an inactive state of the vehicle infotainment system.

19. The method of claim 14, wherein the passive driver impairment detection system comprises a touch-based system configured to direct light towards a tissue of the driver, determine blood alcohol content of the driver in response to the light received after interaction with the tissue, and determine whether the blood alcohol content exceeds a predetermined level.

20. The method of claim 14, wherein the passive driver impairment detection system comprises a breath-based system configured to draw a breath of exhaled air from the driver, direct a light through the breath of air, determine blood alcohol content of the driver in response to the light received after interaction with the breath of air, and determine whether the breath alcohol content exceeds a predetermined level.

21. A method for controlling a passive driver impairment detection system in a vehicle, comprising the steps of:

detecting an off state of a vehicle ignition system, the off state of the vehicle ignition system is indicative of i) an absence of an individual within or approaching the vehicle and ii) a lack of intent of the individual to approach the vehicle;

detecting an inactive state of a vehicle remote starting system, the inactive state of the vehicle remote starting system indicative of the absence of the individual within or approaching the vehicle and the lack of intent of the individual to approach the vehicle;

transmitting a deactivation signal to the passive driver impairment detection system upon detection of the off state of the vehicle ignition system and the inactive state of the vehicle remote starting system, wherein the passive driver impairment detection system is provided to detect an impairment of the individual who intends to operate the vehicle; and transitioning the passive driver impairment detection system from an active state to an inactive state responsive to the deactivation signal;

wherein the transition from the active state to the inactive state only occurs when both the off state of the vehicle ignition system and the inactive state of the vehicle remote starting system corroborate each other and confirm i) and ii).

22. The method of claim 21, further comprising the step of determining a duration since the vehicle ignition system entered the off state and wherein the transmitting step comprises transmitting the deactivation signal only upon detection of the off state of the vehicle ignition system and the inactive state of the vehicle remote starting system and the duration exceeding a predetermined duration.

23. The method of claim 21, further comprising the step of detecting a state of a vehicle occupant monitoring system indicative of the absence of the individual within or approaching the vehicle and the lack of intent of the individual to approach the vehicle and wherein the transmitting step comprises transmitting the deactivation signal only upon detection of the off state of the vehicle ignition system and the inactive state of the vehicle remote starting system and the state of the vehicle occupant monitoring system indicative of the absence of the individual within or approaching the vehicle and the lack of intent of the individual to approach the vehicle.

\* \* \* \* \*